(12) United States Patent
Lee et al.

(10) Patent No.: US 11,143,534 B2
(45) Date of Patent: Oct. 12, 2021

(54) MICRONEEDLE PROBE DEVICE FOR MEASURING SAP FLOW RATE OF PLANT, AND METHOD FOR MEASURING SAP FLOW RATE OF PLANT BY USING SAME

(71) Applicants: Seoul National University R&DB Foundation, Seoul (KR); Republic Of Korea (Management: Rural Development Administration), Jeonju-si (KR)

(72) Inventors: Jung Hoon Lee, Seoul (KR); Sang Woong Baek, Seoul (KR); Eun Yong Jeon, Seoul (KR); Seung Yul Choi, Seoul (KR); Kyoung Sub Park, Gyeongsangnam-do (KR); Joon Kook Kwon, Gyeongsangnam-do (KR); Kyung Hwan Yeo, Gyeongsangnam-do (KR); In Ho Yu, Gyeongsangnam-do (KR); Jae Han Lee, Gyeongsangnam-do (KR)

(73) Assignees: Seoul National University R&DB Foundation, Seoul (KR); Republic Of Korea Rural Development Administration, Jeonju-si (KR)

( * ) Notice: Subject to any disclaimer, the term of this patent is extended or adjusted under 35 U.S.C. 154(b) by 215 days.

(21) Appl. No.: 16/310,103

(22) PCT Filed: Jun. 14, 2017

(86) PCT No.: PCT/KR2017/006217
§ 371 (c)(1),
(2) Date: Dec. 14, 2018

(87) PCT Pub. No.: WO2017/217773
PCT Pub. Date: Dec. 21, 2017

(65) Prior Publication Data
US 2019/0257681 A1 Aug. 22, 2019

(30) Foreign Application Priority Data

Jun. 14, 2016 (KR) .................. 10-2016-0074015
Apr. 3, 2017 (KR) .................. 10-2017-0043259

(51) Int. Cl.
*G01F 1/69* (2006.01)
*G01N 33/00* (2006.01)

(52) U.S. Cl.
CPC .......... *G01F 1/69* (2013.01); *G01N 33/0098* (2013.01)

(58) Field of Classification Search
CPC ................... G01F 1/68–699; G01N 33/0098
See application file for complete search history.

(56) References Cited

U.S. PATENT DOCUMENTS

| 4,745,805 | A | | 5/1988 | Granier | |
|---|---|---|---|---|---|
| 5,763,775 | A | * | 6/1998 | Sato | ............ G01F 1/6842 73/204.26 |
| 9,857,391 | B2 | * | 1/2018 | Shimokawa | ........... A01G 22/00 |

FOREIGN PATENT DOCUMENTS

| JP | 2004085507 A | 3/2004 |
|---|---|---|
| JP | 2008233047 A | 10/2008 |

(Continued)

OTHER PUBLICATIONS

International Search Report and Translation Application No. PCT/KR2017/006217 Completed: Sep. 21, 2017; dated Sep. 21, 2017 5 pages.

(Continued)

*Primary Examiner* — Justin N Olamit
(74) *Attorney, Agent, or Firm* — Whitmyer IP Group LLC (57) ABSTRACT

According to an exemplary embodiment, a microneedle probe device for measuring a sap flow rate of a plant includes: a substrate, of which at least a part is inserted into a plant, and a thickness and a width are microscales; a single (Continued)

metal wire provided on the substrate; a power source, which applies a current to the metal wire for a predetermined time and heats the metal wire; and a processor, which calculates a flow rate of sap through a movement of heat generated in the metal wire according to a flow of the sap within the plant.

7 Claims, 3 Drawing Sheets

(56) References Cited

FOREIGN PATENT DOCUMENTS

| | | | |
|---|---|---|---|
| JP | 2009031014 A | * | 2/2009 |
| JP | 2014211407 A | | 11/2014 |
| KR | 2015145810 A | | 8/2015 |

OTHER PUBLICATIONS

Written Opinion of the International Searching Authority Application No. PCT/KR2017/006217 dated Sep. 21, 2017 6 pages.

Chinese Office Action Application No. 201780043730.1 Completed: Apr. 9, 2020 7 Pages.

Long, Qiubo, et al.; "Review on the development and application of sap flow gauge"; Journal of Water Resources & Water Engineering, vol. 23, No. 4; Aug. 2012; 6 Pages.

* cited by examiner

SAP FLOW

Figure 3

MICRONEEDLE PROBE DEVICE FOR MEASURING SAP FLOW RATE OF PLANT, AND METHOD FOR MEASURING SAP FLOW RATE OF PLANT BY USING SAME

TECHNICAL FIELD

A description below relates to a microneedle probe device for measuring a sap flow rate of a plant, and a method of measuring a sap flow rate of a plant by using the same.

BACKGROUND ART

Environmental variables of a plant growth model directly affects the output and the quality of a plant. Examples of the environmental information of the plant, which mainly affect the plant growth, include temperature, sap flow (SF), and electrical conductivity (EC). Such primary environmental variables of the plant are used to control other factors: water supply schedule, temperature and light amount control, fertilizer supply timing, and the amount of fertilizer to be supplied, etc., leading to the key factors on the plant growth model.

The measured variables of the plant growth model have been limited to external environmental ones such as temperatures, humidity. The methods of internal variables were mostly destructive, indirect, or the like. Traditional methods include measuring the electrical conductivity by using moisture in soil, metered water consumption, and the use of plant samples made as sap. However, these methods have failed to provide sufficient conditions in acquiring direct or detailed information for accurately predicting plant activities.

As a technology for measuring a flow of sap of a plant, for example, a technology of inserting a probe into a stem of a plant has been developed, but the technology uses a device in the form of an invasive probe.

As the methods of measuring a sap flow, there have been used (i) a heat pulse (HP) technology which applies a periodic heat pulse to a plant by using an invasive probe, and calculates flow density by detecting a movement of the heat pulse in accordance with a sap flow in the plant by using a separate temperature probe, (ii) a heat dissipation (HD) technology which continuously applies heat to a plant by using an invasive probe, and measures and calculates, from a temperature difference, a degree to which the heat is dissipated at night in the case of absence of the sap flow and the case of presence of the sap flow, (iii) a heat field deformation (HFD) technology which configures an invasive probe having a temperature measuring probe and a heater probe, and calculates sap flow density by measuring, by using the temperature measuring probe, a degree to which a heat field, which is created by heat generated by a heater at a center, is deformed due to a sap flow, and (iv) a stem heat balance (SHB) technology which uses a temperature difference between upper and lower portions of a stem which is caused by a sap flow and heat generated by a heater installed outside the stem of the plant.

However, because the technologies use the probe which is configured in an invasive form to the extent that the needle has a diameter of 1 to 5 mm, these technologies are limitedly only to a certain types of trees, and it is difficult to insert the invasive probe into plants such as fruits and vegetables, e.g., tomato, sweet pepper, and flowers. In addition, because a measurement device is large in size, expensive, and complicated, there is a problem in that it is difficult to apply the measurement device to various sites of one crop or to various crops at one time, and as a result, it is disadvantageous in aspects of securing reliability of a measurement result and obtaining a statistical results due to the small number of samples.

Innovations in agriculture have been rapidly promoted in virtue of developments of various types of scientific technologies starting with biology. The technology related to the monitoring of plant growth should also benefit from the innovative technologies such as information and communication technology (ICT), micro electro mechanical systems (MEMS), and nanotechnologies.

There is a need for a development of a technology capable of measuring biological information of various plants including trees by using a minimally invasive technology, and to this end, it is necessary to implement a precision measurement technology using the MEMS technology.

More specifically, to meet the needs of minimum invasiveness, the size of a sensor to be inserted into a plant needs to be decreased to a microscale level. Such a microneedle probe needs to be manufactured by using the MEMS technology based on a silicon processing technology, leading to a shape, a size, and the like of the microneedle probe that will interact with the plant tissue sustainably.

SUMMARY

Technical Problem

An exemplary embodiment described herein is to provide a technology, which directly and minimum invasively measures a temperature within a plant and a sap flow rate essentially required for determining a growth model of a plant from the plant and is applicable to plants, such as fruits and vegetables including tomato plants and sweet peppers, and flowers, as well as trees.

Another exemplary embodiment described herein is to provide a technology, which makes a measurement device in a microscale or compact enough to be easily applied to several parts of a crop or several crops at the same time without providing excessive heat, thereby securing measurement reliability.

Technical Solution

According to an exemplary embodiment, a microneedle probe device for measuring a sap flow rate of a plant includes: a substrate, of which at least a part is inserted into a plant, and a thickness and a width are microscales; a single metal wire provided on the substrate; a power source, which applies a current to the metal wire for a predetermined time and heats the metal wire; and a processor, which calculates a flow rate of sap through a movement of heat generated in the metal wire according to a flow of the sap within the plant.

Further, the number of metal wires provided may be two or more, and the plurality of metal wires may be disposed on the substrate while being spaced apart from each other in a longitudinal direction of the inserted part of the substrate, so that the flow rate of the sap is measured at a plurality of places.

Further, the metal wire may have a portion extended in a direction orthogonal to a flow direction of the sap.

Further, the power source may periodically apply a current to the metal wire to make a heat pulse be generated in the metal wire.

Further, the processor may include: a resistance measuring module, which measures resistance of the metal wire and a change in the resistance; a temperature calculating module, which calculates a change in a temperature of the metal wire based on the change in the resistance of the metal wire; and a flow rate calculating module, which calculates the flow rate of the sap based on the change in the temperature of the metal wire.

Further, the substrate may have: a thin portion, of which one end portion is sharply formed and which is inserted into the plant; and a thick portion, which is positioned at a side opposite to the thin portion and has a larger thickness than a thickness of the thin portion, and a width of one end portion of which at a side of the thin portion is increased in a direction away from the thin portion.

According to another exemplary embodiment, a method of measuring a sap flow rate of a plant includes: inserting a microneedle probe device into a plant, the microneedle prove device including a substrate having a thickness and a width of a microscale and a single metal wire provided on the substrate; heating the metal wire by applying a current to the metal wire for a predetermined time; and calculating a flow rate of sap through a movement of heat generated in the metal wire according to a flow of the sap within the plant.

Further, the method may further include generating a heat pulse in the metal wire by periodically applying a current to the metal wire after a termination of the predetermined time.

Further, the calculating of the flow rate of the sap may include: measuring a change in resistance of the metal wire; calculating a change in a temperature of the metal wire based on the change in the resistance of the metal wire; and calculating the flow rate of the sap based on the change in the temperature of the metal wire.

Advantageous Effects

According to the exemplary embodiments described herein, it is possible to reliably measure a flow rate of sap of a plant and a temperature inside a plant body through a microneedle probe, which is minimally invasively applicable to a plant.

Further, the kind of plant, of which a flow rate of sap is measurable, may be extended from trees to crops, of which diameters of stems are small and which are not hard, such as fruits and vegetables including tomato plants and sweet peppers, and flowers without the needs for excessive heating.

Furthermore, it is possible to measure a flow rate of sap at several places of one crop, and measure flow rates of sap in several crops at the same time, thereby further improving reliability of a measurement value.

DETAILED DESCRIPTION OF THE INVENTION

Best Mode

According to an exemplary embodiment, a microneedle probe device for measuring a sap flow rate of a plant includes: a substrate, of which at least a part is inserted into a plant, and a thickness and a width are microscales; a single metal wire provided on the substrate; a power source, which applies a current to the metal wire for a predetermined time and heats the metal wire; and a processor, which calculates a flow rate of sap through a movement of heat generated in the metal wire according to a flow of the sap within the plant.

Further, the number of metal wires provided may be two or more, and the plurality of metal wires may be disposed on the substrate while being spaced apart from each other in a longitudinal direction of the inserted part of the substrate, so that the flow rate of the sap is measured at a plurality of places.

Further, the metal wire may have a portion extended in a direction orthogonal to a flow direction of the sap.

Further, the power source may periodically apply a current to the metal wire to make a heat pulse be generated in the metal wire.

Further, the processor may include: a resistance measuring module, which measures resistance of the metal wire and a change in the resistance; a temperature calculating module, which calculates a change in a temperature of the metal wire based on the change in the resistance of the metal wire; and a flow rate calculating module, which calculates the flow rate of the sap based on the change in the temperature of the metal wire.

Further, the substrate may have: a thin portion, of which one end portion is sharply formed and which is inserted into the plant; and a thick portion, which is positioned at a side opposite to the thin portion and has a larger thickness than a thickness of the thin portion, and a width of one end portion of which at a side of the thin portion is increased in a direction away from the thin portion.

According to another exemplary embodiment, a method of measuring a sap flow rate of a plant includes: inserting a microneedle probe device into a plant, the microneedle prove device including a substrate having a thickness and a width of a microscale and a single metal wire provided on the substrate; heating the metal wire by applying a current to the metal wire for a predetermined time; and calculating a flow rate of sap through a movement of heat generated in the metal wire according to a flow of the sap within the plant.

Further, the method may further include generating a heat pulse in the metal wire by periodically applying a current to the metal wire after a termination of the predetermined time.

Further, the calculating of the flow rate of the sap may include: measuring a change in resistance of the metal wire; calculating a change in a temperature of the metal wire based on the change in the resistance of the metal wire; and calculating the flow rate of the sap based on the change in the temperature of the metal wire.

Mode For Carrying Out the Invention

Hereinafter, particular exemplary embodiments will be described in detail with reference to the accompanying drawings. Further, a detailed description of known configurations or functions incorporated herein will be omitted when it is judged that the detailed description may make the subject matter of the exemplary embodiments unclear.

In the meantime, singular expressions used herein include plural expressions unless they have definitely opposite meanings in the context. In addition, unless explicitly described to the contrary, the word "comprise" and variations such as "comprises" or "comprising", will be understood to imply the inclusion of stated elements but not the exclusion of any other elements.

Figure 1:
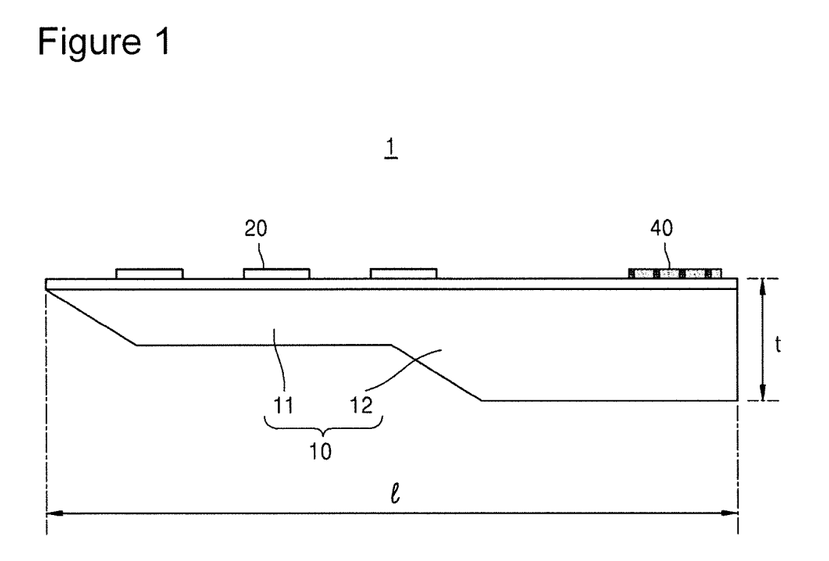
FIG. 1 is a schematic lateral cross-sectional view of a microneedle probe device for measuring a sap flow rate of a plant according to an exemplary embodiment.
Figure 2:
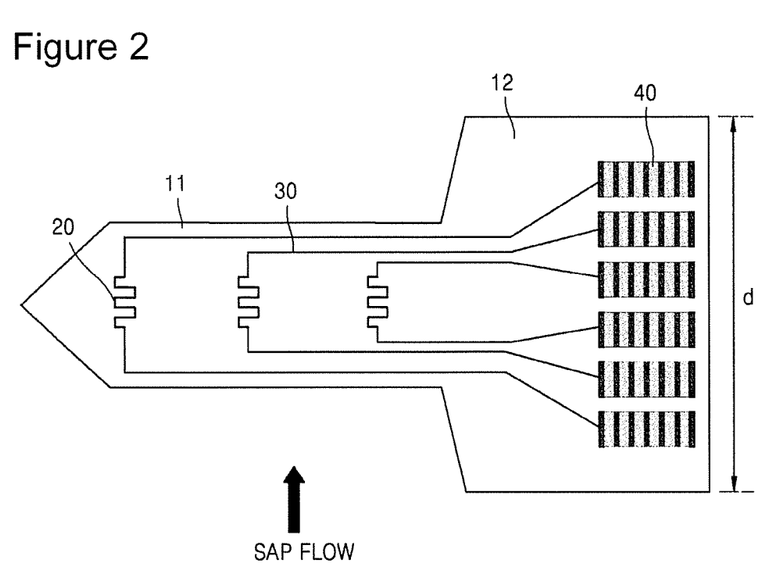
FIG. 2 is a schematic top plan view of the microneedle probe device for measuring a sap flow rate of a plant of FIG. 1.

FIGS. 1 and 2 are schematic lateral cross-sectional view and top plan view of a microneedle probe device 1 (hereinafter, referred to as a "microneedle probe") for measuring a sap flow rate of a plant according to an exemplary embodiment, respectively. The microneedle probe 1 according to the present exemplary embodiment may be manufactured by a micro electro mechanical systems (MEMS) process based on silicon, and may be inserted into a neck portion (vessel) of a plant and minimally invasively measure a flow rate of sap flowing within the neck portion.

The microneedle probe 1 may include a substrate 10. The substrate 10 may be manufactured of silicon through the MEMS process as described above. The substrate 10 may have a thin portion 11 inserted into a plant and a thick portion 12 at a side opposite to the thin portion, and the thin portion 11 may have a relatively small thickness, and the thick portion 12 may have a relatively large thickness (see FIG. 1). As described above, the thin portion 11 is thinner than the thick portion 12, so that the microneedle probe 1 may be easily inserted into tissue inside the plant, and the thick portion 12 is formed to be thicker than the thin portion 11, so that rigidity of the substrate 10 may be secured.

Further, one end portion at the side of the thin portion 11 inserted into the plant is formed to be sharp to the extent to an atomic level, so that the microneedle probe 1 may be easily inserted into the plant. The degree of sharpness of the one end portion may be adjusted by a semiconductor dry etching process or silicon impurity doping and selective etching.

In the meantime, a width of the thick portion 12 may be larger than a width of the thin portion 11 (see FIG. 2). For example, a width of one end portion of the thick portion 12 at the side of the thin portion 11 may be the same as a width of the thin portion 11 or may be increased toward the thick portion 12. Accordingly, a tapered inclined surface may be formed in the one end portion of the thick portion 12. By the structure, it is possible to secure rigidity so that the microneedle probe 1 is not broken when the microneedle probe 1 is inserted into the plant and measure a flow rate of sap.

The substrate 10 of the microneedle probe 1 according to the present exemplary embodiment has a small size of a microscale, so that it is possible to measure a flow rate of sap under a minimally invasive condition. As a size of the substrate 10, a length l may be 1 to 6 mm, a thickness t may be 100 to 200 μm, and a width d may be 200 to 400 μm.

Unlike a probe in the related art, which has a diameter of 1 to 5 mm and is applicable only to large and hard trees, the microneedle probe 1 according to the present exemplary embodiment may be inserted into fine tissue of a plant and maintained, so that the microneedle probe 1 is applicable even to a plant, of which a stem is thinner than a tree, such as a fruit vegetable plant including a tomato plant and a paprika plant or flowers.

A metal wire 20 for measuring a flow rate of sap may be provided on the substrate 10. The metal wire 20 may be formed of, for example, platinum, and may be formed in a metal micro pattern. When a current is applied to the metal wire 20, the metal wire 20 may be heated, which will be described below, and heat generated in the metal wire 20 may move in the same direction as that of sap by a flow of the sap. Accordingly, the sap may take the heat of the metal wire 20. The change in the temperature of the metal wire 20 is represented as a change in resistance of the metal wire 20, and the change in the temperature may be calculated by reading the change in the resistance, and further, a flow rate of sap may be calculated through the change in the temperature.

Further, the metal wire 20 may be disposed to be extended in a direction orthogonal to a flow direction of the sap (see FIG. 2). For example, as illustrated in FIG. 2, the metal wire 20 is formed of a single wire, and may have a plurality of portions extended in the direction orthogonal to the flow direction of the sap. When the metal wire 20 is configured as described above, the heat generated in the metal wire 20 is better radiated by the flow of the sap, so that accuracy of the measurement of the change in the resistance of the metal wire 20, and ultimately, the measurement of the flow rate of sap may be improved.

In the meantime, as illustrated in the drawing, the number of metal wires 20 provided may be two or more, and the plurality of metal wires 20 may be disposed while being spaced apart from each other in a longitudinal direction of the substrate 10. In this case, it is possible to measure a flow rate of sap at several points of the plant, thereby improving reliability of a measurement value.

A power source (not illustrated) may be disposed on the substrate 10 or disposed while being spaced apart from the substrate 10, and may apply a current to the metal wire 20 through a BUS line 30 mounted on the substrate 10. The BUS line 30 may be a low-resistance BUS line, and may be connected with the power source through contact pads 40.

In the meantime, the power source may apply a current to the metal wire 20 only for a predetermined time, and further, the power source may periodically apply a current to the metal line 20 so that a heat pulse is generated in the metal line 20.

A processor (not illustrated) may include a resistance measuring module, a temperature calculating module, and a flow rate calculating module. The modules are the examples, and may have circuit forms. The resistance measuring module may measure a change in resistance of the metal wire 20 by heating or cooling of the metal wire 20. The temperature calculating module may calculate a change in a temperature of the metal wire 20 by using the change in the resistance. In this case, the temperature calculating module may calculate a change in a temperature according to a change in resistance by using a temperature coefficient of resistance. The flow rate calculating module may calculate a flow rate of sap by using the change in the temperature.

In the meantime, the processor may be understood as a concept including the resistance measuring module, the temperature calculating module, and the flow rate calculating module, and is not essentially limited to the form of a single physical chip. When the processor is mounted to the substrate 10, the resistance measuring module, the temperature calculating module, and the flow rate calculating module may be provided while being integrated in one chip or being divided into two or more chips. Otherwise, in the state where the resistance measuring module is mounted to the substrate 10, at least one of the temperature calculating module and the flow rate calculating module may also be disposed while being spaced apart from the substrate 10. In this case, the resistance and the change value of the resistance of the metal wire 20 measured by the resistance measuring module may be transmitted to the outside of the substrate 10 by a wired or wireless scheme by a communication module (not illustrated).

A cover (not illustrated) may be provided on the substrate 10 and cover the entirety or a part of the metal wire 20. The cover may be provided, for example, in the form of a thin film, and may cover the metal wire 20 and mechanically, electrically, and chemically protect the metal wire 20. Further, the cover may have an insulating property.

When the cover is provided in the form of the thin film, a material of the cover may be an inorganic material, such as a silicon oxide, a silicon nitride, an aluminum oxide, a hafnium oxide, and may also be a water repellent organic material, such as polytetrafluoroethylene (PTFE) and cyclic transparent optical polymer (CYTOP). The cover may include a plurality of inorganic material layers, a plurality of organic material layers, or the form, in which an inorganic material layer and an organic material layer are combined, in order to improve insulating performance.

For example, a silicon nitride may be deposited on the metal wire 20 by a chemical vapor deposition (CVD) scheme. Further, in order to minimize an influence by a defect in a process, a silicon nitride layer and a silicon oxide layer may be alternately deposited. In this case, even though any one layer has a defect, another layer may serve as an insulating film. Otherwise, a defect of an inorganic material layer may be supplemented by using atomic layer deposition. The atomic layer deposition achieves very high uniformity of a deposited thin film, so that the atomic layer deposition may fill a crack of a silicon nitride thin film or a defect, such as a pin hole, and improve a quality of an insulating thin film. For another example, in order to improve insulating performance, a composite layer of an organic thin film and an inorganic thin film may be used. An organic material thin film layer, such as PTFE and CYTOP, may be formed on an inorganic material thin film layer by a method of dip coating, spin coating, vapor deposition, and the like. A hydrophobic organic thin film may prevent a liquid from permeating to the metal wire 20 to improve performance of an insulating thin film. Hereinafter, an operation of the microneedle probe 1 according to the present exemplary embodiment will be described.

The power source may apply a current for the metal line 20 for a predetermined time, and accordingly, the metal wire 20 may be heated. Further, as described above, the power source may periodically apply a current to the metal wire 20, and in this case, a heat pulse may be generated in the metal wire 20. For example, when the power source supplies power of 100 mW to the metal wire 20 for 30 seconds, a temperature of the metal wire 20 may rise compared to a temperature of a neighboring area. Then, when a predetermined time elapses, the quantity of heat generated in the metal wire 20 and the quantity of heat radiated to the neighboring area become balanced, so that the metal wire 20 may be maintained at a predetermined temperature (reach a stagnation point of a temperature). Then, when power is blocked, the temperature of the metal wire 20 may fall again and be equal to the temperature of the neighboring area after a predetermined time. When a flow rate of sap is large, heat radiation incurred by convection is large, a calorie generated in the metal wire 20 and a radiated calorie may be balanced at a low temperature. In this case, a time taken for the balance may be relatively short. When a flow rate of sap is low or there is no flow of sap, heat radiation by convection is little, so that heat may be balanced at a high temperature. Then, in this case, a time taken for the balance may be relatively long.

In the meantime, the application of a voltage lower than 0 V to the metal wire 20 may be more advantageous in preventing electrochemical oxidization of the metal wire 20. For example, when a voltage (for example, 5 V) higher than 0 V is applied to the metal wire 20, a portion of the metal wire 20, which is in contact with tissue of the plant, has a relatively high potential compared to a plant body in the case where the metal wire 20 is exposed under the condition of the non-existence or a defect of the cover, so that electrochemical oxidization is accelerated, and there is a possibility in that a lifespan is decreased. In the meantime, a voltage less than 0 V is applied to the metal wire 20, a potential of the metal wire 20 exposed under the condition of the non-existence or a defect of the cover is lower than that of a plant body, so that an oxidization action generated in the metal wire 20 may be suppressed, thereby leading an increase in a lifespan.

In the case of the present exemplary embodiment, the change in the temperature of the metal wire 20 may be calculated from a change in resistance of the metal wire 20. As described above, the resistance measuring module of the processor may measure resistance of the metal wire 20 changed according to a change in a temperature, and the temperature calculating module may calculate a change in a temperature of the metal wire 20 by using a temperature coefficient of resistance based on a resistance change value.

For example, a Wheatstone bridge circuit may be used for measuring resistance of the metal wire 20. The metal wire 20 having a predetermined resistance value and three other resistance wires having similar resistance values to the predetermined resistance value may form a quadrangle. When four resistance values are the same, a potential difference between two intermediate points of the Wheatstone bridge circuit is 0. When a resistance value of the metal wire 20 is changed by heating of the metal wire 20 and the like, a potential difference is generated between the two intermediate points. Then, when the potential difference generated as described above is measured, a change in resistance may be inversely calculated. For reference, when a potential difference is amplified by using a differential amplifier, it is possible to more precisely measure a change in resistance.

For another example, a constant current circuit may be used for measuring a change in resistance of the metal wire 20. A circuit, in which a predetermined current flows, by using a constant current regulator and the like, is manufactured, and the metal wire 20 may be connected to the circuit. The predetermined current flows regardless of resistance of the metal wire 20, so that when a voltage applied to the metal wire 20 is measured, it is possible to inversely calculate a resistance value of the metal wire 20. In this case, when a voltage signal is amplified by using an amplifier, it is also possible to more precisely measure a change in a resistance value.

In the meantime, when the change in the resistance of the metal wire 20 and the temperature coefficient of resistance (TCR) are recognized, a temperature change amount of the metal wire 20 may be recognized. For example, when initial resistance of 100Ω of the metal wire 20 formed of gold (Au) increases to 101Ω by a change in a temperature of the metal wire 20, a temperature change amount of the metal wire 20 in this case may be obtained by using Equation 1 below.

$$T2 - T1 = \frac{R2 - R1}{R1} * \frac{1}{\alpha} \qquad \text{Equation 1}$$

Herein, T1 and T2 may mean an initial temperature and a temperature after a change of the metal wire 20, respectively, R1 and R2 may mean initial resistance and resistance after a change of the metal wire 20, respectively, and a may mean a temperature coefficient of resistance of the metal wire 20. When the resistance of the metal wire 20 increases from 100Ω to 101Ω, a temperature coefficient α of resistance of gold is known as 0.0034, so that a change in a temperature of the metal wire 20 may be about 2.94°.

Next, the flow rate calculating module may calculate a flow rate of sap based on a temperature change value of the metal wire 20. A correlation between the flow rate of sap and the change in the temperature of the metal wire 20 may be expressed by Equation 2 below.

$$u = a \cdot \left(\frac{\Delta T_M - \Delta T}{\Delta T}\right)^b \quad \text{Equation 2}$$

Herein, u is a flow rate (m³/m² s) of sap and ΔT is a temperature difference between the case where power is applied to the metal wire 20 and the case where power is not applied to the metal wire 20 in a heat balance state. $\Delta T_M$ is a temperature difference value (that is, a maximum value of ΔT) of the metal wire 20 when there is no flow of sap. a and b are constants, and are experimentally obtained. ΔT and $\Delta T_M$ may be obtained by turning on or off the power source supplied to the metal wire 20.

The microneedle probe 1 according to the present exemplary embodiment is a single wire system using the single metal wire 20 mounted on the single substrate 10, so that a structure thereof may be simple. The simplification of the structure is a very important element in a structure of a microscale, thereby being advantageous in an aspect of easiness of implementation.

Further, unlike the related art, in which a heater probe and a temperature measuring probe are separately provided, it is possible to measure emitted heat and measure a temperature only using the single metal wire 20 on the single substrate 10, thereby also contributing to simplifying the structure.

Similarly, a probe for applying power and a temperature measuring probe are not separately provided, but a change in a temperature of the metal wire 20 may be measured by a scheme of adjusting power by using only the single substrate 10, thereby being advantageous in an aspect of simplification of the structure.

Figure 3:
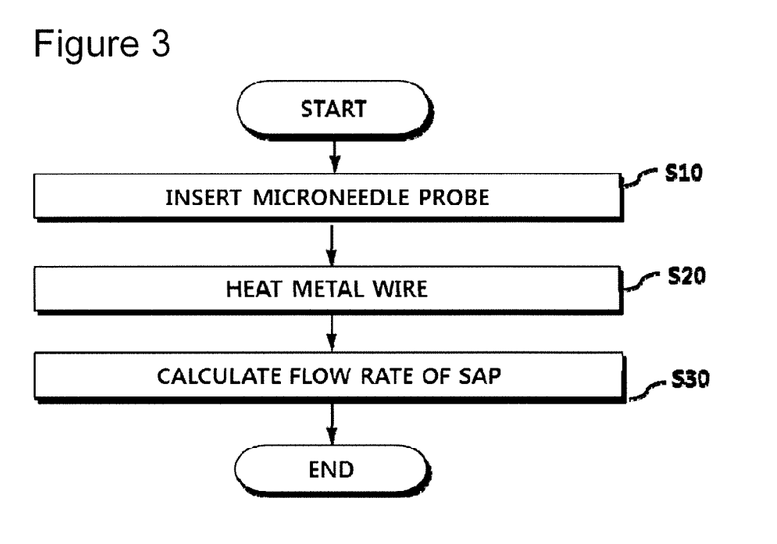
FIG. 3 is a flowchart of a method of measuring a sap flow rate of a plant according to an exemplary embodiment.

FIG. 3 is a flowchart of a method of measuring a sap flow rate of a plant according to an exemplary embodiment. Hereinafter, a method of measuring a sap flow rate will be described with reference to FIG. 3 together with FIGS. 1 and 2.

In order to measure a sap flow rate of a plant, first, the microneedle probe 1 may be inserted into a plant (S10). As described above, the microneedle probe 1 may include the substrate 10 and the metal wire 20 provided on the substrate 10. Then, the substrate 10 may include the thin portion 11 and a thick portion 12, and at least a part of the thin portion 11 may be inserted into a neck portion of a stem of the plant. One end portion of the thin portion 11 is sharply formed, so that the thin portion 11 may be easily inserted. In the meantime, the microneedle probe 1 may be inserted into the plant so that at least a part of the metal wire 20 is extended in a direction orthogonal to a flow of the sap.

Then, the metal wire 20 may be heated by applying a current to the metal wire 20 for a predetermined time by controlling the power source (S20). As described above, the power source may apply a current to the metal wire 20 again after a predetermined time after the elapse of the predetermined time. The power source periodically applies the current to the metal wire 20 as described above, so that a heat pulse may be generated in the metal wire 20.

Next, a speed of the sap may be finally calculated by detecting a movement of heat generated in the metal wire 20 (S30). Particularly, heat moves in a flow direction of the sap by the flow of the sap, and a temperature of the metal wire 20 is changed by the movement of the heat. A flow rate may be calculated by recognizing a change in the temperature, but in the present exemplary embodiment, it is described that a change in the temperature is recognized by recognizing a change in resistance of the metal wire 20. That is, a separate temperature measuring probe is not required. For example, a change in resistance of the metal wire 20 may be measured by using a relation between a temperature and a resistance (a temperature coefficient of resistance and the like), and next, the change in the temperature of the metal wire 20 may be calculated based on the change in the resistance. When the change in the temperature of the metal wire 20 is calculated, a flow rate of sap may be calculated based on the calculated change in the temperature.

In the foregoing exemplary embodiments, some examples of the present technical spirit are described, and the scope of the present technical spirit is not limited to the foregoing exemplary embodiments, and various changes, modifications, or substitutions may be made within the scope of the present technical spirit by those skilled in the art. For example, the configurations and the characteristics described together in the specific exemplary embodiment may be dispersed from each other and carried out, and the configurations and the characteristics described in each of the different exemplary embodiments may be carried out in a combination form. Similarly, the configurations and the characteristics described in each claim may be dispersed from each other and carried out, or combined and carried out. Further, it shall be considered that all the carrying-out of the configurations and the characteristics belong to the scope of the present technical spirit.

The invention claimed is:

1. A microneedle probe device for measuring a sap flow rate of a plant, the microneedle probe device comprising:
   a substrate, of which at least a part is insertable into a plant, and a thickness and a width are microscales;
   two or more metal wires provided on the substrate, each of the metals wire provides for a measurement to determine a flow rate of sap at the respective metal wire, each of the metal wires is disposed on the substrate while being spaced apart from each other in a longitudinal direction of the at least a part of the substrate, so that the flow rate of the sap is measured at a plurality of places;
   a power source, which applies a current to the metal wires for a predetermined time and heats the metal wires; and
   a processor, which calculates the flow rate of the sap at each metal wire through a movement of heat generated in the respective metal wire according to a flow of the sap within the plant;
   wherein the processor includes:
   a resistance measuring module which measures resistance of each metal wire and a change in the resistance of each metal wire;
   a temperature calculating module which calculates a change in a temperature of each metal wire based on the change in the resistance of the respective metal wire; and
   a flow rate calculating module which calculates the flow rate of the sap at each metal wire based on the change in the temperature of the respective metal wire.

2. The microneedle probe device of claim 1, wherein the metal wire has a portion extended in a direction orthogonal to a flow direction of the sap.

3. The microneedle probe device of claim 1, wherein the power source periodically applies a current to the metal wire to make a heat pulse be generated in the metal wire.

4. The microneedle probe device of claim 1, wherein the substrate has:
- a thin portion, of which one end portion is sharply formed and which is inserted into the plant; and
- a thick portion, which is positioned at a side opposite to the thin portion and has a larger thickness than a thickness of the thin portion, and a width of one end portion of which at a side of the thin portion is increased in a direction away from the thin portion.

5. A method of measuring a sap flow rate of a plant, the method comprising:
- inserting a microneedle probe device into a plant, the microneedle probe device including a substrate having a thickness and a width of a microscale and two or more metal wires provided on the substrate, each of the metal wires provides for a measurement to determine a flow rate of sap at the respective metal wire, each of the metal wires is disposed on the substrate while being spaced apart from each other in a longitudinal direction of the at least a part of the substrate, so that the flow rate of the sap is measured at a plurality of places;
- heating the metal wires by applying a current to the metal wires for a predetermined time; and
- calculating the flow rate of the sap at each metal wire through a movement of heat generated in the respective metal wire according to a flow of the sap within the plant,
- wherein the calculating of the flow rate of the sap includes:
- measuring a change in resistance of each metal wire;
- calculating a change in a temperature of each metal wire based on the change in the resistance of the respective metal wire; and
- calculating the flow rate of the sap at each metal wire based on the change in the temperature of the respective metal wire.

6. The method of claim 5, further comprising:
- generating a heat pulse in the metal wire by periodically applying a current to the metal wire after a termination of the predetermined time.

7. A microneedle probe device for measuring a sap flow rate of a plant, the microneedle probe device comprising:
- a substrate having only one part insertable into a plant, the substrate having a thickness and a width of a microscale;
- a plurality of metal wires disposed on said only one part insertable into the plant, each of the metal wires provides for a measurement to determine a flow rate of sap at the respective metal wire, each of the metal wires is disposed on the substrate while being spaced apart from each other in a longitudinal direction of said only one part of the substrate, so that the flow rate of the sap is measured at a plurality of places;
- a power source, which applies a current to the metal wires for a predetermined time and heats the metal wires; and
- a processor, which calculates the flow rate of the sap at each metal wire through a movement of heat generated in the respective metal wire according to a flow of the sap within the plant;
- wherein the processor includes:
- a resistance measuring module which measures resistance of each metal wire and a change in the resistance of each metal wire;
- a temperature calculating module which calculates a change in a temperature of each metal wire based on the change in the resistance of the respective metal wire; and
- a flow rate calculating module which calculates the flow rate of the sap at each metal wire based on the change in the temperature of the respective metal wire.

* * * * *